United States Patent [19]

Mitscher et al.

[11] Patent Number: 4,471,052
[45] Date of Patent: Sep. 11, 1984

[54] BIOSYNTHESIS OF SIMPLIFIED ANTHRACYCLINES

[75] Inventors: Lester A. Mitscher, Lawrence, Kans.; Daniel Lednicer, Dublin, Ohio

[73] Assignee: Adria Laboratories, Inc., Columbus, Ohio

[21] Appl. No.: 340,139

[22] Filed: Jan. 18, 1982

[51] Int. Cl.$^3$ ...................... C12P 19/56; C12N 15/00; C12R 1/465
[52] U.S. Cl. .................................. 435/78; 435/172.1; 435/886
[58] Field of Search ................. 435/78, 169, 172, 886, 435/172.1

[56] References Cited

U.S. PATENT DOCUMENTS 3,590,028 6/1971 Arcamone et al. ................... 435/78
4,267,312 5/1981 Oki et al. ............................. 435/78
4,309,503 1/1982 Cassinelli et al. ................... 435/172
4,337,312 6/1982 Oki et al. ............................ 435/172

FOREIGN PATENT DOCUMENTS 30255 6/1981 European Pat. Off. ............. 435/78

OTHER PUBLICATIONS

Oki et al., J. Antibiotics, 33(11): 1331–1340 (1980).
Yoshimoto et al., J. Antibiotics, 33(10): 1199–1201, 1158–1166 (1980).

Primary Examiner—Esther M. Kepplinger
Attorney, Agent, or Firm—Biebel, French & Nauman

[57] ABSTRACT

Chemically simplified versions of intermediates on the identified biosynthetic pathway to daunomycin are bioconverted to active analogues of naturally occurring antibiotics.

9 Claims, No Drawings

BIOSYNTHESIS OF SIMPLIFIED ANTHRACYCLINES

BACKGROUND OF THE INVENTION

The present invention relates to a microbiological process for producing anthracycline anticancer antibiotics. More particularly, it relates to a process in which chemically simplified versions of intermediates on the identified biosynthetic pathway to daunomycin are bioconverted to active analogues of naturally occurring antibiotics.

Anthracyclines and, more notably, doxorubicin, daunorubicin, carminomycin and aclacinomycin have emerged as important chemotherapeutic agents in the treatment of a broad spectrum of human cancers. Understandably, their synthesis has attracted much attention.

Conventionally, anthracycline antibiotics are produced by aerobic fermentation of strains of Streptomyces. One of the drawbacks of conventional fermentations is that they are incapable of yielding analogues of the antibiotics when they are allowed to run their natural course. As a result, attempts have been made to develop more versatile syntheses for the antibiotics by chemical routes. Preferably, syntheses can be developed which can be readily modified to yield the anitbiotics and analogues which are more potent and less toxic.

The majority of the chemical routes which have been developed to date are only partially successful. Typically, they involve numerous reaction steps and they yield the compounds in only very small amounts. Several of the known synthetic approaches involve steps which are difficult to carry out chemically and provide intermediates in low yields. Many chemical routes break down at the glycosidation step. Of necessity any chemical synthesis must end by coupling the anthracycline aglycone with the amino sugar which constitutes the antibiotic. While in some of the literature this reaction is reported to occur in a rather high percent yield, in actuality the laboratory procedures which have been developed provide only a few milligrams of product.

Thus, although the chemical structure of these antibiotics have been known for some time, there is still a need for a versatile and effective synthesis of these antibiotics and, more importantly, a synthesis capable of yielding desired product in large amounts that is suitable for industrial application.

Recently, studies have been directed to the biosynthetic pathway to daunomycin in various Streptomyces. While some portions of the pathway remain unidentified, it is now apparent that aklavinone and $\epsilon$-rhodomycinone are on the pathway. Yoshimoto et al, *The Journal Of Antibiotics,* Vol. 33, No. 10, Oct. 1980, pp. 1158–65, proposes a pathway which proceeds via a hypothetical decaketide through aklavinone to $\epsilon$-rhodomycinone and from there via decarbomethoxylation of the C-10 position to daunomycin. There is also evidence that carminomycin is reached in the pathway.

The identified pathway is revealed as having the following enzymic capacities:

11—hydroxylation
10—decarbomethoxylation
4—methylation
7—glycosylation
7—reduction
13—hydroxylation and ketonization.

While these pathways and enzymic capabilities are evident in the literature, with limited exceptions, prior efforts have concentrated on the pathway itself and the production of natural occurring products. Its ability to produce structural analogous of the natural products has not been defined.

SUMMARY OF THE INVENTION

A principal object of the present invention is to provide an expedient synthesis for anthracycline antibiotics which are simplified versions of naturally occurring antibiotics.

The present invention makes active anticancer antibiotics available through syntheses from chemically simplified analogues of identified intermediates on the biosynthetic pathway which are readily synthesizable in good yields by known chemical reaction routes. While numerous antibiotics can be obtained by the invention process, among its principal targets are 4-demethoxy adriamycin, 4-demethoxy-11-desoxy adriamycin, 4-demethoxy daunomycin, 4-demethoxy-11-desoxy daunomycin and 4-demethoxy aclacinomycin. Each of the above compounds has been established to exhibit anticancer activity, particularly to lymphoblastic and myeloblastic leukemia.

In accordance with the invention chemically simplified versions of the anthracyclinones identified on the Streptomyces pathway of daunomycin are added to a growing culture of selected Streptomyces strains where the antibiotic is completed or an intermediate is obtained that requires only minimal chemical modification to yield the antibiotic. The invention process is advantageous because, the synthesis is not burdened and attenuated by difficult and low yield chemistry. Furthermore, it obviates most of the need for stereospecificity in the chemical reactions that are relied upon for the starting materials since the bioconversions involved in the invention process are inherently stereospecific and able to reject the stereospecifically inactive portion of a starting racemate.

One reaction which is extremely difficult to carry out in yields suitable for the pharmaceutical industry is coupling the anthracyclinone and the sugar constituents of the antibiotic. In accordance with the invention processes glycosidation is accomplished biosynthetically. Thus, anthracyclines in which the C-7 position is unsubstituted or hydroxy or keto substituted are bioconverted to the therapeutically effective glycoside by subjecting them to the enzymic activity of an appropriate anthracycline producing Streptomyces strain. It is also unnecessary to resolve an intermediate which is racemic at C-7 since the preferred strain selectively glycosidate the $\alpha$-isomer. This provides chemically modified antibiotics in higher yields than are possible by an entirely chemical approach.

The starting anthracyclines used in the invention are those readily obtained by conventional synthesis and obtained in high yields. In one embodiment of the present invention the antibiotics are prepared from anthracyclines in which the D-ring is symmetrical and unsubstituted. The chemical synthesis of such compounds is streamlined and can be accomplished on an industrial scale since there is no regiochemistry involved in the formation of the D-ring. When fed to the appropriate Streptomyces strain, these anthracyclines generate the 4-demethoxy family of antibiotics which seem to possess all the activity of adriamycin and are less toxic.

Another class of compounds readily synthesized by the invention process are the 4-demethoxy-11-desoxy compounds. These compounds are unsubstituted at both the C-4 and C-11 positions and in accordance with the present invention they are obtained by bioconversion of starting materials which are fairly easily obtained in workable quantities by known chemistry. Typically, these antibiotics are obtained from anthracyclines which are unsubstituted at C-4 and C-11.

Another advantage of the invention synthetic process is that it is not necessary to provide a starting anthracycline with a C-9 substituent having the capacity to chemically transform to the critical C-9 carbonyl functionality in the antibiotic. In yielding daunomycin Streptomyces convert a simple 9-ethyl group in aklavinone or ε-rhodomycinone to a 9-methylcarbonyl group. Thus, 9-ethyl starting anthracyclines can be used in the present invention instead of the 9-substituted carbonyl precursors conventionally relied upon in a totally chemical approach. Furthermore, the synthesis is not ladened by the multi-step chemistry required to protect the 9-carbonyl group throughout the subsequent synthesis and generate the appropriate orientation of the hydroxy and carbonyl substitutes at the 9-position.

The starting compounds suitable for producing anthracycline antibiotics in accordance with the present invention are represented by the formula I:

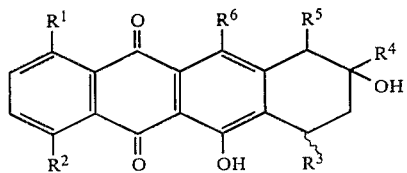

Where
R$^1$ is hydrogen or hydroxy;
R$^2$ is hydrogen, hydroxy or C1-4 alkoxy
R$^3$ is hydrogen, hydroxy, or keto
R$^4$ is C1-4 alkyl, COCH$_3$, or CH(OH)CH$_3$
R$^5$ is hydrogen or COOR$^7$
R$^6$ is hydrogen or hydroxy, and
R$^7$, when R$^5$ is COOR$^7$, is hydrogen or C1-3 alkyl
with the proviso that the compound of formula I is not aklavinone, ε-rhodomycinone, or ε-pyrromycinone.

One of the preferred classes of anthracyclines for use in the present invention are herein referred to as aklavinone-like compounds and are compounds of the formula II:

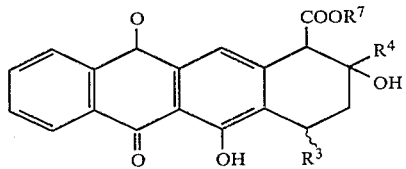

where R$^3$, R$^4$ and R$^7$ are defined as above. Of the compounds of formula II those in which R$^3$ is hydroxy or keto are preferred for use in the invention.

Another class of anthracyclines which is particularly useful are herein referred to as rhodomycinone-like compounds and are compounds of the formula III:

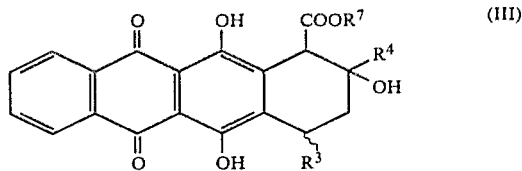

where R$^3$, R$^4$ and R$^7$ are defined as before. Those compounds in which R$^3$ is hydroxy or keto and R$^4$ is ethyl appear particularly useful.

Still another class of compounds that can be bioconverted to active antibiotics in the invention are so-called daunomycinone-like compounds of the formula IV:

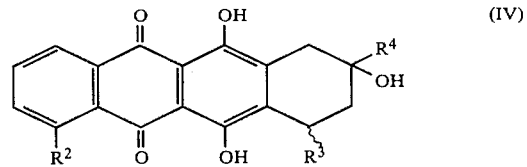

where R$^2$, R$^3$ and R$^4$ are defined as in formula I. R$^2$ is preferably hydrogen and R$^3$ is preferably hydroxy or keto.

Of the above compound, compound of the formula V below and their 7-keto analogues appear to be particularly useful substrates for biosynthetic elaboration in accordance with this invention:

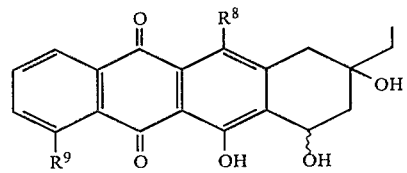

wherein:
(i) R$^8$=R$^9$=H
(ii) R$^8$=OH, R$^9$=H
(iii) R$^9$OH, R$^8$=H
(iv) R$^8$=R$^9$=OH.

These and other compounds are converted to simplified versions of the naturally occurring antibiotics by adding them to a growing culture of a strain of Streptomyces as described in more detail below.

DETAILED DESCRIPTION OF THE INVENTION

A principal advantage of the present invention is that effective antibiotics are obtained from simplified intermediates. Various anthracyclines can be used as the starting material or precursor of the present invention. Generally, the target antibiotics are produced from tetracyclines possessing a reduced or non-aromatic A-ring. One embodiment of the invention process is particularly directed to producing 4-demethoxy anthracycline antibiotics from the corresponding 4-demethoxy aglycone. These compounds have been found to be less toxic than their natural analogues.

In general, the starting anthracyclines used in the present invention have been encountered as intermediates in the reported chemical syntheses for daunomycinone and aklavinone. Otherwise, they can be prepared by synthetic modifications of the reported syntheses that are easily accomplished.

The compounds of formula I where $R^5$ is hydrogen and the aklavinone-like compounds of formula II are typically obtained by reactions analogous to those reported by Kishi et al, Kende et al and Confalone et al, *J.A.C.S.*, 103, 4247; 4248; and 4251 (1981) for the synthesis of alkavinone. See also *C&E News*, July 20, 1981, p. 31. While aklavinone compounds of the formula II do not have a 4-hydroxy group as does aklavinone their synthesis can be accomplished in the same manner as the aforementioned syntheses using the unsubstituted analogues of the reported starting materials. Because C-4 substitution does not enter into the reported aklavinone synthesis, its absence does not interfere with obtaining the desired product. Thus, the formula II compounds can be obtained in the Confalone synthesis from monomethyl phthalate and in the Kishi synthesis from 2-bromo-1,4-naphthoquinone.

The rhodomycinone of formula I and formula III are merely 11-hydroxy analogues of the alkavinones and are generally simpler to synthesize. This is particularly true in the case of the 4-desoxy rhodomycin which is symmetric about each of the B, C and D rings. They are perhaps most easily synthesized by the Confalone synthesis from 1,4 dihydroxy7-ethyl-5,6,7,8 tetrahydronaphthalene. The dihydroxy tetrahydro naphthalene condenses with 2-carbomethoxy, 5-methoxy benzoic acid. It will be appreciated by those skilled in the art that the synthesis from compounds of the formula III is a sub-synthesis of the synthesis from formula II compounds where the Streptomyces has 11-hydroxylation capacity.

Daunomycinone-like compounds of formula IV are available through various syntheses. Alexander et al, U.S. Pat. No. 4,244,880 teaches a synthesis of the compounds of formula VI:

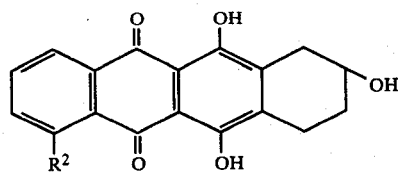

VI where $R^2$ is defined as above. This compound is readily converted to the compound of formula VII

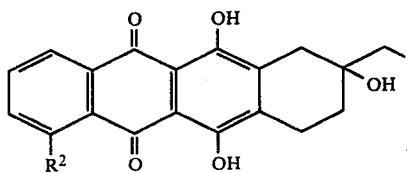

VII which is a useful starting material for the invention process. Where a 7-hydroxyl is required, this is added by halogenation followed by solvolysis and epimerization much as taught by Kinde et al, *J. Amer. Chem. Soc.*, 98, 1967 (1976).

Daunomycin can be derived from the above compound in good yields when it is added to a strain having the capacity to convert C-13 to carbonyl and to add the amino sugar. Adriamycin is prepared using an adriamycin producing strain having 13-hydroxylation capacity in addition to the biosynthetic capacities already mentioned.

While the Alexander et al objective was a complete chemical synthesis of daunomycinone, those skilled in the art will appreciate that the synthesis simplifies when the D ring is unsubstituted yielding the corresponding 4-demethoxy starting anthracycline.

In addition to the Alexander et al synthesis, compounds of the formula IV can also be synthesized by the method of Raynolds et al *Tetrahedron Letters*, No. 28, pp. 2383–86 (1977).

In accordance with the invention process, compounds chemically synthesized as above, are subjected to Streptomyces strains and bioconverted to active antibiotics. The identified biosynthetic pathway indicates that these strains have the capacity to reduce the keto group at C-7 and add sugar, methylate the hydroxyl group at C-4, remove an alkoxy carbonyl group at C-10, and transform a C-13 alkyl carbon to a ketocarbon. Some introduce a phenolic OH at C-11. Depending on the starting material and the strain selection, some or all of these conversions may take place.

All of the invention syntheses proceed via bioglycosidation of the aglycone. In some case the microorganism accepts the 7-desoxy analogue ($R^3=H$), but as a general rule the strains used require the hydroxyl group or a keto group at the C-7 position of the intermediate to couple the amino sugar and form the antibiotic. Thus $R^3$ is preferably hydroxy or keto in formulae I-V and more preferably hydroxy. As indicated above, in most cases it is not necessary to resolve a C-7 racemate, but where the α isomer is readily available synthetically it will afford improved overall yields.

Sometimes the invention bioconversion yields a mixture containing di and trisaccharides at the 7-position. When this occurs the bioconversion product can be subjected to mild hydrolysis to remove the extra sugars. Typically this is conducted under very mild acid conditions so that the sugar coupled directly to the aglycone is not removed.

Another enzymic activity of Streptomyces is methylation of a phenolic OH at C-11. When this is undesired, as in the case of producing the 4-demethoxy compounds, the anthracycline subjected to the activity of the Streptomyces should be unsubstituted at C-4.

The microorganisms used in carrying out the bioconversions of the present invention are anthracycline producing strains of Streptomyces which will accept the compounds described above and convert them to the desired analogues. The strains used may occur naturally or be mutants obtained chemically or by radiation. Strains which are known to have this ability are Streptomyces peucetius carneus (ATCC No. 21354), Streptomyces peucetius caesius (ATCC No. 27952), Streptomyces caeruleus (ATCC No. 27421), Streptomyces galilaceus, Streptomyces peucetius (ATCC No. 29050) and Streptomyces coeruleorubidus (ATCC No. 13740).

The bioconversions are carried out under aerobic conditions at a temperature, humidity and on a nutrient which will support fermentation of the organism in a manner well known in the art. A typical growth medium useful in the present invention contains 1.5% soluble starch, 1% glucose, 3% soybean meal, 0.1% yeast extract, 0.1% $K_2HPO_4$, 0.1% $MgSO_4.7H\ O$, 0.3% NaCl, 0.007% $CuSO_4.5H_2O$, 0.001% $FeSO_4.7H_2O$, 0.0008% $MnCl_2.4H_2O$ and 0.0002% $ZnSO_4.7H_2O$ in tap water, pH 7.4.

The culture containing the microorganism and the antibiotic precursor are cultivated, typically, at about 28° for several days. After cultivation the biconversion products are removed from the fermentation medium by extraction. Numerous solvents may be used for the extraction such as chloroform, ethyl acetate, a mixture of chloroform and methanol, etc. Thereafter, the conversion products are separated and the desired products isolated by silica gel chromatography in a standard manner.

Having described my invention in detail and by reference to preferred embodiments thereby it will be apparent to those skilled in the art that numerous variations and modifications thereof are possible without departing from the invention as claimed.

What is claimed is:

1. A process for producing 4-demethoxy derivatives of daunomycin, adriamycin, aclacinomycin, 11-desoxyadriamycin, or 11-desoxydaunomycin which comprises:

introducing a 4-demethoxy derivative of an anthracyclinone occurring on the identified biosynthetic pathway of daunomycin to a fermentation medium of an anthracycline producing strain of Streptomyces capable of glycosylating said anthracyclinone and producing a 4-demethoxy derivative of daunomycin, adriamycin, aclacinomycin, 11-desoxyadriamycin, or 11-desoxydaunomycin, said strain being selected from the group consisting of *S. peucetius corneus, S. peucetius caesius, S. caeruleus, S. peucetius, S. coeruleorubidus* and chemical or radiation-induced mutants thereof, cultivating said medium, removing the conversion products from said medium, and isolating the 4-demethoxy derivative of daunomycin, adriamycin, aclacinomycin, 11-desoxyadriamycin, or 11-desoxydaunomycin.

2. The process of claim 1 wherein said 4-demethoxy derivatives of an anthracyclinone is represented by the formula I

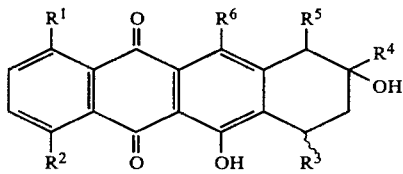

wherein $R^1$ is hydrogen or hydroxy, $R^2$ is hydrogen, $R^3$ is, hydroxy or keto, $R^4$ is C 1-4 alkyl, $R^5$ is hydrogen or $COOR^7$, $R^6$ is hydrogen or hydroxy and $R^7$ is hydrogen or C 1-3 alkyl.

3. The process of claim 2 wherein said 4-demethoxy derivatives of an anthracyclinone is represented by the formula II

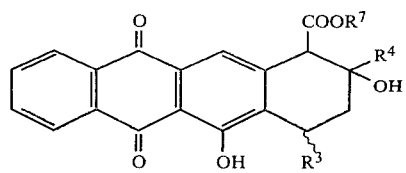

where $R^3$, $R^4$ and $R^7$ are defined as in claim 2.

4. The process of claim 3 wherein $R^3$ is hydroxy.

5. The process of claim 2 wherein said 4-demethoxy derivatives of an anthracyclinone is represented by the formula III

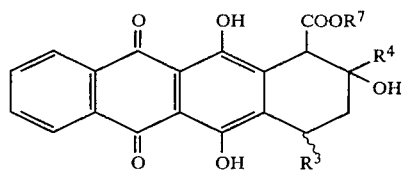

wherein $R^3$, $R^4$ and $R^7$ are defined as in claim 2.

6. The process of claim 5 wherein $R^3$ is hydroxy and $R^4$ is ethyl.

7. The process of claim 2 wherein said 4-demethoxy derivatives of an anthracyclinone is represented by the formal IV

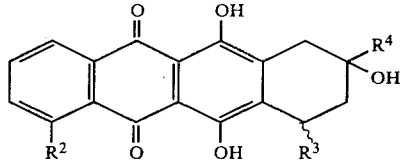

where $R^2$, $R^3$ and $R^4$ are defined as in claim 2.

8. The process of claim 7 wherein $R^3$ is hydroxy.

9. The process of claim 2 wherein said 4-demethoxy derivatives of anthracyclinone is a compound of the forúmula V below:

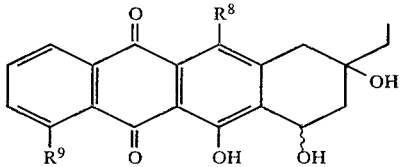

wherein:
(i) $R^8 = R^9 = H$
(ii) $R^8 = OH$, $R^9 = H$.

* * * * *